US010175250B2

(12) United States Patent
Da Silva et al.

(10) Patent No.: US 10,175,250 B2
(45) Date of Patent: Jan. 8, 2019

(54) NITRATED CARDIAC TROPONIN I AS A BIOMARKER OF CARDIAC ISCHEMIA

(76) Inventors: Gabriela Venturini Da Silva, São Paulo (BR); Alexandre Da Costa Pereira, São Paulo (BR); José Eduardo Krieger, São Paulo (BR); Deborah Schechtman, São Paulo (BR); Pedro Lemos, São Paulo (BR); Jeane Mike Tsutsui, São Paulo (BR); Valdemir Melechco Carvalho, São Paulo (BR); Karina Helena Morais Cardozo, São Paulo (BR)

(*) Notice: Subject to any disclaimer, the term of this patent is extended or adjusted under 35 U.S.C. 154(b) by 0 days.

(21) Appl. No.: 13/493,488

(22) Filed: Jun. 11, 2012

(65) Prior Publication Data
US 2013/0330744 A1    Dec. 12, 2013

(51) Int. Cl.
G01N 33/68    (2006.01)
C07K 14/47    (2006.01)
C07K 7/06     (2006.01)
C07K 7/08     (2006.01)
C07K 16/18    (2006.01)
C12Q 1/37     (2006.01)

(52) U.S. Cl.
CPC .......... G01N 33/6887 (2013.01); C07K 7/06 (2013.01); C07K 7/08 (2013.01); C07K 14/4716 (2013.01); C07K 16/18 (2013.01); C12Q 1/37 (2013.01); G01N 2800/324 (2013.01); G01N 2800/325 (2013.01)

(58) Field of Classification Search
CPC ........ G01N 33/6887; G01N 2800/324; G01N 2800/325; C07K 14/4716; C07K 7/06; C07K 7/08; C07K 16/18; C12Q 1/37
See application file for complete search history.

(56) References Cited

U.S. PATENT DOCUMENTS 5,834,220 A * 11/1998 Wicks et al. ............... 435/7.92
2002/0156005 A1 * 10/2002 Meyers ......................... 514/12
2005/0176081 A1 * 8/2005 Reginster et al. ........... 435/7.93
2011/0033868 A1 * 2/2011 Bottari ......................... 435/7.1

FOREIGN PATENT DOCUMENTS

WO    WO 2010138899 A2 * 12/2010    ............. G01N 30/72

OTHER PUBLICATIONS

Mihm et al., Effects of peroxynitrite on isolated cardiac trabeculae: selective impact on myofibrillar energetic controllers, Biochimie 85 (2003) 587-596.*
Waters, Increasing the Sensitivity of MRM Measurements for Tryptic Peptides Using Xevo TQ-S, pp. 1-2, 2010.*
Amoresano et al., A Rapid and Selective Mass Spectrometric Method for the Identification of Nitrated Proteins, From: Methods in Molecular Biology, vol. 477: Advanced Protocols in Oxidative Stress I, vol. 477, 2008, pp. 15-29.*
Bast et al., Translational Crossroads for Biomarkers, Clin Cancer Res 2005; 11(17), 6103-6108.*
LaBaer et al., So you want to look for biomarkers, Journal of Proteome Research 2005; 4, 1053-1059.*
Baker, In Biomarkers We Trust, Nature Biotechnology 2005; 23(3) 297-304.*
Qu et al., A Novel Competitive ELISA for Both Free and Protein-Bound Nitrotyrosine, Hybridoma and Hybridomics, 22(6), 2003, 401-406.*
Shishehbor et al., Association of Nitrotyrosine levels with Cardiovascular disease and Modulation by Statin Therapy, JAMA 2003, 289(13), 1675-1680.*

* cited by examiner

Primary Examiner — Andrea S Grossman
(74) Attorney, Agent, or Firm — Banner & Witcoff, Ltd.

(57) ABSTRACT

The present invention relates to the identification of a novel biomarker for cardiac ischemia: nitrated cardiac troponin I. The present invention also provides methods for the identification and use of a nitrated cardiac troponin as a biomarker for the diagnosis, prognosis and treatment management of myocardial ischemia, with and without necrosis of heart muscle.
Diagnosis and prognosis is conducted by determining the amount of nitrated cardiac troponin I in serum samples of subjects and the ratio of nitrated cardiac troponin I to non-nitrated cardiac troponin I in serum samples of subjects. This biomarker can be detected by immunoassay techniques and tandem mass spectrometry. The present invention further relates to peptides, antibodies, compositions, methods, techniques, tests and kits for the identification and quantification of nitrated cardiac troponin I in samples of subjects.

16 Claims, 11 Drawing Sheets
Specification includes a Sequence Listing.

SEQUENCE LISTING

```
<160> NUMBER OF SEQ ID NOS: 7

<210> SEQ ID NO 1
<211> LENGTH: 211
<212> TYPE: PRT
<213> ORGANISM: Homo sapiens

<400> SEQUENCE: 1

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser Leu
    210
```

```
<210> SEQ ID NO 2
<211> LENGTH: 9
<212> TYPE: PRT
<213> ORGANISM: Homo sapiens

<400> SEQUENCE: 2

Ala Tyr Ala Thr Glu Pro His Ala Lys
 1               5

<210> SEQ ID NO 3
<211> LENGTH: 9
<212> TYPE: PRT
<213> ORGANISM: Homo sapiens

<400> SEQUENCE: 3

Ala Tyr Ala Thr Glu Pro His Ala Lys
 1               5

<210> SEQ ID NO 4
<211> LENGTH: 20
<212> TYPE: PRT
<213> ORGANISM: Homo sapiens

<400> SEQUENCE: 4

Pro Ala Pro Ile Arg Arg Arg Ser Ser Asn Tyr Arg Ala Tyr Ala Thr
 1               5                  10                  15

Glu Pro His Ala
            20

<210> SEQ ID NO 5
<211> LENGTH: 5
<212> TYPE: PRT
<213> ORGANISM: Homo sapiens

<400> SEQUENCE: 5

Ala Tyr Ala Thr Glu
 1               5

<210> SEQ ID NO 6
<211> LENGTH: 4
<212> TYPE: PRT
<213> ORGANISM: Homo sapiens

<400> SEQUENCE: 6

Pro His Ala Lys
 1

<210> SEQ ID NO 7
<211> LENGTH: 7
<212> TYPE: PRT
<213> ORGANISM: Homo sapiens

<400> SEQUENCE: 7

Ala Thr Glu Pro His Ala Lys
 1               5
```

NITRATED CARDIAC TROPONIN I AS A BIOMARKER OF CARDIAC ISCHEMIA

This application incorporates by reference the contents of a 2.82 kb text file created on Jan. 22, 2013 and named "13493488sequencelisting.txt," which is the sequence listing for this application.

FIELD OF THE INVENTION

The present invention relates to the identification of a novel biomarker for cardiac ischemia: nitrated cardiac troponin I. The present invention also provides methods for the identification and use of a nitrated cardiac troponin as a biomarker for the diagnosis prognosis and treatment management of cardiac ischemia. The present invention further relates to peptides, antibodies, compositions, methods, techniques and tests for the identification and quantification of nitrated cardiac troponin I in the serum of subjects.

BACKGROUND OF THE INVENTION

Acute coronary syndromes are among the major causes of mortality and morbidity in the world. Millions of patients are treated annually with chest pain of acute onset. In this situation it is extremely important to quickly identify when this pain is due to myocardial ischemia so that adequate care may be started. Myocardial ischemia is a clinical condition characterized by reduced blood supply to the heart. Currently, there are no effective diagnostic methods for this disease. Presently, the diagnosis is based on common noninvasive tests such as exercise testing, myocardial perfusion scintigraphy, however, these tests are expensive and have limited sensitivity and specificity (Parikh; Lemos, 2006). Also, a large part myocardial ischemia patients go undiagnosed due to the absence of accurate diagnostic tests for myocardial ischemia without necrosis of the heart muscle (Pope at al, 2000; McCaig; Burt, 2002; Lloyd-Jones et al, 2009).

In the United States, the FDA has approved the use of ischemia modified albumin (IMA) as a marker for ischemia. This marker consists of the loss of affinity of albumin for cobalt after myocardial ischemia. However, this marker is not sufficiently specific, as it has been shown to be elevated in several clinical situations such as in renal failure, stroke and heavy-load aerobic exercise (Debashis I, et al, 2004; Lippi, et al, 2005; Morrow, et al, 2007; Singh et al, 2010).

Recently, the use of the levels of cytoplasmic cardiac troponins in serum as markers for myocardial injury has been suggested. Cardiac troponins are specific to cardiac myocytes, however, due to the high sensitivity of the assay, these proteins are also detectable in the serum of healthy patients and in other heart diseases as well as acute coronary syndromes or clinical situations where myocardial ischemia occurs (Eggers, et al, 2009; Reichlin et al, 2009; Masson et al, 2010; Hochholzer et al, 2011).

Thus, the currently available cardiac ischemia markers are either nonspecific because they are present in other organs and tissues other than the myocardium, and/or they are elevatedin other clinical situations other than myocardial ischemia.

Due to the prominent lack of markers of cardiac ischemia, the diagnosis and early treatment may occur at a very late stage in patients with unstable angina. On the other hand, in patients with non-ischemic chest pain, the uncertainty about the diagnosis may require hospital admission for investigation which results in undesirable excessive health care costs.

In addition to emergency testing, an accurate marker of myocardial ischemia is also useful in ambulatory management of patients in the diagnosis of stable angina, especially in association with exercise testing or stress myocardial scintigraphy.

Interestingly, cardiovascular diseases, especially acute coronary syndromes, are strongly associated with an oxidative imbalance, leading to increased free radicals and increased reactive oxygen and nitrogen species. Thus, in such diseases, there is an increase in the production of nitric oxide, superoxide and a change in the antioxidant pathways, leading to nitroxidative and oxidative stress (Levrand et al, 2006; Peluffo, Radi, 2007; Aslan, Dogan, 2011).

As a result of the increase of these reactive species, intermediate species such as peroxynitrite and formed. Peroxynitrite, among other actions, leads to the formation of nitrated proteins by the addition of a $NO_2$ group to the phenolic ring of the tyrosine residues (Ischiropoulos, 2009).

This nitration may alter the protein in several ways: the protein may become resistant to degradation, it may activate the immune system, it may become inactivated or it may acquire a new function. These changes in protein activity can impact the pathophysiology of the cardiovascular system (Abello et al, 2009).

Several proteins have been identified as being nitrated in different compartments of the cardiovascular system, such as fibrinogen, plasmin and Apo-1 in the plasma; Apo-B, cyclooxygenase, prostaglandin synthase and Mn-SOD in the vessel walls; myofibrillar creatine kinase and $\alpha$-actinin in the myocardium. These nitrated proteins were associated to cardiovascular disease (Aslan, Dogan, 2011).

In view of this, nitrated proteins are emerging as new markers for cardiovascular disease. However, protein nitration also occurs in other pathophysiological situations involving increased reactive oxygen and nitrogen species, such as in diabetes, stroke, neurodegenerative diseases, kidney disease and other diseases associated with ischemia/reperfusion and inflammation (Gole et al, 2000; Castegna et al, 2003; Turko et al, 2003, Ahmed et al, 2005; Heffron et al, 2009; Isobe et al, 2009; Choi et al, 2010; Tyther et al, 2011; Piroddi et al, 2011). Thus, in the search for a nitrated biomarker that is specific to cardiovascular disease it is important that the modified protein target is expressed only or mainly in cardiac tissue.

Troponins are cytoplasmic proteins that have specific cardiac muscle isoforms and are found in the circulation in very low concentrations in healthy subjects and that have its concentration increased in situations of stress to the heart muscle, such as necrosis of the cardiomyocytes. Cardiac troponin I is a cytoplasmic protein unique to cardiac myocytes and is one of three subunits that form the troponin protein complex. This subunit is responsible for sensitivity to calcium and regulates muscle contraction. Troponin I binds to actin and inhibits the ATPase activity of actomiosin in the absence of calcium (Bhaysar et al, 1996).

BRIEF SUMMARY OF THE INVENTION

The present invention relates to the identification of a novel biomarker for cardiac ischemia: nitrated cardiac troponin I. The present invention also provides methods for the identification and use of a nitrated cardiac troponin as a biomarker for the diagnosis, prognosis and treatment management of myocardial ischemia, with and without necrosis of heart muscle.

Diagnosis and prognosis is conducted by determining the amount of nitrated cardiac troponin I in serum samples of subjects and the ratio of nitrated cardiac troponin I to non-nitrated cardiac troponin I in serum samples of subjects. This biomarker can be detected by immunoassay techniques and tandem mass spectrometry. The present invention further relates to peptides, antibodies, compositions, methods, techniques and tests for the identification and quantification of nitrated cardiac troponin I in the serum of subjects.

In one embodiment, this invention relates to the identification of a novel biomarker for cardiac ischemia: nitrated cardiac troponin I.

In one embodiment, this invention provides a new useful marker for the diagnosis and quantification of cardiac ischemia and for the diagnosis and prognosis of patients with acute coronary syndrome. This invention also provides methods for using the biomarker for the diagnosis and prognosis of cardiac ischemia.

In one embodiment, this invention relates the identification of nitrated cardiac troponin I, and the use of this molecule or its fragments in the diagnosis, prognosis and treatment of acute coronary syndrome. This molecule or fragments thereof are present in different concentrations in those individuals who do not present myocardial ischemia, compared to those who present myocardial ischemia. This molecule or fragments thereof are present in samples of patients with acute coronary syndrome in concentrations that are directly proportional to the area affected by ischemic myocardial infarction.

In some embodiments, the invention provides a method for the diagnosis, prognosis or selection of best method of treatment of individuals with chronic and acute coronary syndrome that includes: determining the concentration of nitrated cardiac troponin I molecules or peptide fragments derived from this molecule in a sample, determining the concentration of nitrated cardiac troponin I or fragments in a series of individual samples, correlating the concentration with reference values for diagnosis and prognosis and correlating with the area of myocardium affected by ischemia.

In one embodiment, the method comprises the quantification of nitrated cardiac troponin I in the serum and plasma, and its correlation with reference values to determine the diagnosis of cardiac ischemia.

In another embodiment, the method comprises the quantification of nitrated cardiac troponin I in the serum and plasma and the correlation of the values observed with the area of myocardium affected by ischemia.

In another embodiment, the method comprises the quantification of nitrated cardiac troponin I in the serum and plasma, and its correlation with reference values to determine the prognosis of cardiac ischemia.

In another embodiment, the method comprises the quantification of the ratio of nitrated cardiac troponin I to troponin I in f serum or plasma samples and its correlation with the reference values to determine the diagnosis of cardiac ischemia.

In another embodiment, the method comprises the quantification of the ratio of nitrated cardiac troponin I to troponin I in samples of serum or plasma and correlation with the reference values to determine the prognosis of cardiac ischemia.

In another embodiment, the method comprises the quantification of the ratio of nitrated cardiac troponin I to troponin I in serum or plasma samples and correlation of the values with the area affected by myocardial ischemia.

In another embodiment, the method comprises the quantification of nitrated cardiac troponin I in serum or plasma samples and correlation with the status of the acute coronary syndrome.

In another embodiment, the method comprises the quantification of the ratio of nitrated cardiac troponin I to troponin I in serum or plasma samples and correlation with the status of the acute coronary syndrome.

In one embodiment, the method comprises the quantification of peptides from nitrated cardiac troponin I in serum or plasma samples, and correlation with reference values to determine the diagnosis of cardiac ischemia.

In one embodiment, the method comprises the quantification of peptides from nitrated cardiac troponin I in serum or plasma samples and correlation with reference values to determine the prognosis of cardiac ischemia.

In another embodiment, the method comprises the quantification of nitrated cardiac troponin I peptides in serum or plasma samples and correlation of the values with the area affected by myocardial ischemia.

In another embodiment, the method comprises the quantification of the ratio of various peptides from nitrated cardiac troponin I in serum or plasma samples and correlation with the reference values to determine the diagnosis of cardiac ischemia.

In another embodiment, the method comprises the quantification of the ratio of various peptides nitrated cardiac troponin I in serum and plasma samples and correlation of the values with the area of myocardium affected by ischemia.

In another embodiment, the method comprises the quantification of peptides from nitrated cardiac troponin I in serum and plasma samples sand correlation with the status of acute coronary syndrome.

In another embodiment, the method comprises the quantification of the ratios of various peptides from nitrated cardiac troponin I in serum or plasma samples and correlation with the status acute coronary syndrome.

In some embodiments the method comprises the quantification of the ratio of nitrated cardiac troponin I peptides and cardiac troponin I peptides in serum or plasma samples and correlatation with the reference values for diagnosis of cardiac ischemia.

In some embodiments, the method comprises the quantification of the ratio of peptides from nitrated cardiac troponin I to peptides from cardiac troponin I in serum and plasma samples to correlate the values with the area of myocardium affected by ischemia.

In another embodiment, the method comprises the quantification of the ratio of peptides from nitrated cardiac troponin I to peptides from cardiac troponin I in serum or plasma samples and correlation with acute coronary syndrome status.

The invention provides several different methods to quantify the biomarker for diagnosis, prognosis and status of cardiac ischemia. For example, in some embodiments of the invention the quantification of the biomarker is performed by enzymatic digestion followed by liquid chromatography and tandem mass spectrometry (quadrupole TQS).

In another embodiment biomarker quantification is performed by liquid chromatography followed by digestion and analysis by LC-TQS.

In some embodiments of the invention, the biomarker of the invention can be quantified by immunoassay or mass spectrometry. In one embodiment, the invention provides an immunoassay comprising an antibody molecule specific to cardiac troponin I and nitrated peptide fragments specific to cardiac troponin I nitrated. In some embodiments, the invention provides a specific monoclonal antibody to a specific region of nitrated cardiac troponin I, which contains the portion of the nitrated biomarker. For example, the portion of nitrated cardiac troponin I can be specifically detected without cross-reactivity with non-nitrated troponin I. This immunoassay enables the detection of the complete nitrated protein molecule and of the specific fragment containing the nitration.

In some embodiments of the invention, the antibody specific to the region comprises amino acids 16-35 of nitrated cardiac troponin I. In some embodiments of the method the antibody used to detect nitrated cardiac troponin I is polyclonal. In some embodiments of the method the antibody used to detect nitrated cardiac troponin I is monoclonal.

In some embodiments the method includes the capture of nitrated cardiac troponin I or nitrated cardiac troponin I peptides. In some embodiments of the invention, the capture can be performed using paramagnetic beads. In some embodiments of the invention the capture of the molecule is achieved using an antibody. In some embodiments of the invention, the molecule is captured using a monoclonal antibody specific for the region comprising amino acids 16-35 of nitrated cardiac troponin I. In some embodiments of the invention the capture of the molecule is achieved by column chromatography.

In one embodiment, the invention provides methods for determining the course of acute coronary syndrome by quantifying nitrated cardiac troponin I and its peptides, and quantifying the ratio of nitrated cardiac troponin I and total troponin I in a first time and compared with the values obtained in a second time after pharmacological or surgical intervention, or for monitoring disease progression.

In another embodiment, the invention provides methods for monitoring echocardiogram accompanied by some form of pharmacological or physical stress. In this embodiment, the amount of nitrated cardiac troponin I can be determined before the start of the examination, during and after the test. This embodiment can also be performed by determining the amount of peptides from nitrated cardiac troponin I. In this embodiment, it is also possible to quantify the ratio of nitrated cardiac troponin I and total cardiac troponin I in the samples.

In another embodiment, the invention provides methods for monitoring myocardium scintigraphy accompanied by some form of pharmacological or physical stress. In this embodiment, the amount of nitrated cardiac troponin I can be determined before the start of the examination, during and after the test. This embodiment can also be performed by determining the amount of peptides from nitrated cardiac troponin I. In this embodiment, it is also possible to quantify the ratio of nitrated cardiac troponin I and total cardiac troponin I in the samples In another embodiment, the invention provides methods for monitoring nuclear magnetic resonance of the myocardium accompanied by some form of pharmacological or physical stress. In this embodiment, the amount of nitrated cardiac troponin I can be determined before the start of the examination, during and after the test. This embodiment can also be performed by determining the amount of peptides from nitrated cardiac troponin I. In this embodiment, it is also possible to quantify the ratio of nitrated cardiac troponin I and total cardiac troponin I in the samples In another embodiment, the invention provides methods for monitoring ergometry tests. In this embodiment, the amount of nitrated cardiac troponin I can be determined before the start of the examination, during and after the test. This embodiment can also be performed by determining the amount of peptides from nitrated cardiac troponin I. In this embodiment, it is also possible to quantify the ratio of nitrated cardiac troponin I and total cardiac troponin I in the samples.

In some embodiments of the invention, the sample is blood, serum or plasma.

In some embodiments of the invention, the diagnosis, prognosis or the method of treatment is a diagnosis, prognosis or definition of treatment for myocardial infarction.

In some embodiments of the invention the diagnosis, prognosis or method for treatment provides a risk stratification for the level of risk of myocardial infarction.

In some embodiments of the invention the method of diagnosis, prognosis or the method of treatment provides a risk stratification for the level of risk of death.

In some embodiments of the invention, the concentration or range of concentrations of nitrated cardid troponin I provides the diagnosis of myocardial ischemia if the individual has one or more symptoms of myocardial ischemia.

In some embodiments of the invention, these symptoms may comprise be pain and/or pressure in the chest, abnormal ECG, shortness of breath or abnormal enzyme levels.

In some embodiments of the invention, the method for determining the concentration in samples of individuals is performed by comparing the values found for nitrated cardiac troponin I or peptide fragments of nitrated cardiac troponin I with a standard curve of known concentrations of purified nitrated cardiac troponin I or fragments of nitrated cardiac troponin I.

In some embodiments of the invention, the method for determining the concentration of nitrated cardiac troponin I or fragments of nitrated cardiac troponin I in samples of individuals is performed by comparing the values found for nitrated cardiac troponin I or peptide fragments to nitrated cardiac troponin I with a standard curve of known concentrations of purified nitrated cardiac troponin I or fragments of nitrated cardiac troponin I.

In some embodiments of the invention the method for determining the concentration of nitrated cardiac troponin I or fragments of nitrated cardiac troponin in samples of individuals is performed by comparing the values found for nitrated cardiac troponin I or peptide fragments of nitrated cardiac troponin I with a internal standard of known concentrations. In some embodiments, the internal standard consists of the peptide AYATEPHAK (SEQ ID NO:3) isotopically labeled with $^{13}C$ and $^{15}N$.

In some embodiments of the invention the method for determining the concentration of nitrated cardiac troponin I or fragments of nitrated cardiac troponin in samples of individuals is performed by comparing the values found for nitrated cardiac troponin I or peptide fragments of nitrated cardiac troponin I with a internal standard of known concentrations. In some embodiments, the internal standard consists of the peptide AYATEPHAK (SEQ ID NO:3) isotopically labeled with $^{13}C$ and $^{15}N$.

In some embodiments of the invention, the change in levels of nitrated cardiac troponin I nitrated may indicate acute coronary syndrome. In some embodiments of the invention, the change in levels of nitrated cardiac troponin I may indicate chronic coronary disease. In some embodiments of the invention, the change in nitrated cardiac troponin I levels may indicate cardiotoxicity.

The invention further relates to the use of nitrated cardiac troponin I or fragments thereof as a marker in diagnosis and prognosis of cardiac ischemia and of acute coronary syndrome.

In the context of this invention cardiac ischemia refers to but is not limited to acute cardiac ischemia, chronic cardiac ischemia, chronic coronary disease and acute coronary syndrome.

In the context of this invention acute coronary syndrome refers to but is not limited to unstable angina, myocardial infarction without ST-segment elevation and myocardial infarction with ST-segment elevation.

This invention also relates to a kit for diagnosing cardiac ischemia and/or acute coronary syndrome, comprising an isolated nitrated cardiac troponin and/or cardiac troponin I or fragments thereof, and a system for detecting the peptide bound to an antibody for said peptide and/or a substrate for immobilizing the peptide.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings, wherein:

FIG. 11A, nitrated troponin I sequenced peptides. FIG. 11B, Coverage map of nitrated cardiac troponin I.

DETAILED DESCRIPTION OF THE INVENTION

Figure 1:
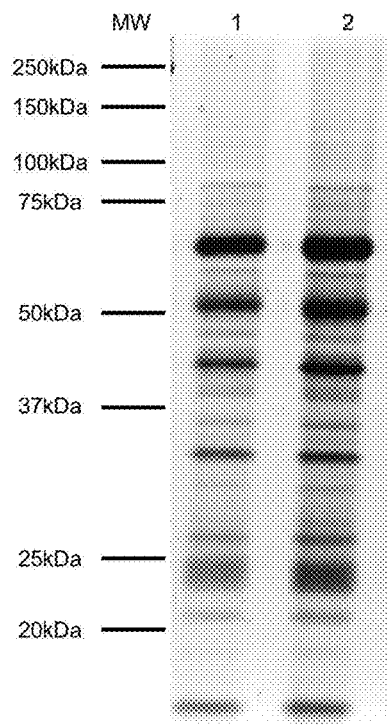
FIG. 1 is a 12% SDS-PAGE gel electrophoresis showing nitrated proteins enriched from serum. MW-molecular weight marker. kDa—kiloDaltons. 1—nitrated serum proteins from the control animal. 2-nitrated serum proteins from the animal with myocardial ischemia.
Figure 2:
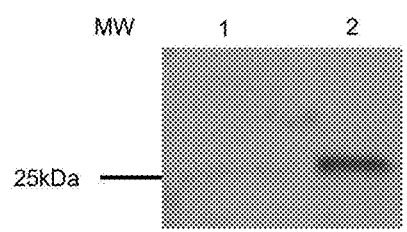
FIG. 2 shows a Western blot detection of nitrated cardiac troponin I (25 kDa) in a pig serumsample after myocardial ischemia. Nitrated proteins enriched from serum. MW— molecular weight marker. kDa—kiloDaltons. 1—nitrated serum proteins from the control animal; 2—nitrated serum proteins from y the myocardial ischemia animal.

Nitrated Cardiac Troponin I as a Biomarker for Myocardial Ischemia and Acute Coronary Syndrome The biomarker of the present invention, nitrated cardiac troponin I was characterized by immunoprecipitation followed by detection of nitrated cardiac troponin I by Western blot.

First we performed the enrichment of nitrated serum proteins by immunoprecipitation using antibody anti-nitrotyrosine (modified Parastatidis, I et al, 2007). Then nitrated serum proteins were loaded on gel electrophoresis SDS-PAGE followed by transfer to PVDF membrane. The membrane was then incubated with anti-cardiac troponin I, showing stained positive for cardiac troponin I.

The nitrated cardiac troponin I of the present invention may be further characterized by the detection of peptide fragments by mass spectrometry ESI-TQ coupled to liquid chromatography. These features provide a method of determining the presence and concentration this protein in biological samples.

Nitrated cardiac troponin may also be characterized by immunoassay with monoclonal antibody specific for nitrated cardiac troponin I. This method is also used to determine the concentrations of nitrated cardiac troponin I samples of individuals.

The biomarker of the present invention may be detected in several ways and in different types of biological samples.

Nitrated cardiac troponin is preferentially detected in serum or plasma from individuals by immunoassay techniques or mass spectrometry. Nitrated cardiac troponin I can also be detected in heart tissue as a result of biopsy, through Western blot techniques and by confocal microscopy.

Using immunoenrichment and immunodetection techniques it was possible to determine that cardiac troponin I is nitrated after myocardial ischemia. Furthermore, it is possible to detect said nitrated cardiac troponin I in the serum of individuals after the ischemic event. Thus we have discovered a new biomarker for cardiac ischemia.

Detection by Mass Spectrometry

In some embodiments the biomarker of this invention can be detected by mass spectrometry.

Mass spectrometry, coupled or not to liquid chromatography, is a technique that can distinguish and quantify proteins by monitoring specific peptide fragments, their retention time and the ratio between them.

This technique is able to differentiate between similar proteins with different post-translational modifications such as phosphorylation, glycosylation, lipidation, methylation, cysteinylation, acetylation, oxidation, nitration and sulphonation. The mass spectrometer can be coupled to one or several types of liquid chromatographies that can aid in the detection of specific molecules or fragments thereof. The liquid chromatography coupled to the mass spectrometer may be used to carry out various types of separation techniques based on properties such as hydrophobicity, affinity, ion exchange, immunoaffinity, among others.

In some embodiments of the invention, mass spectrometry is used coupled to liquid chromatography to quantify the concentrations of nitrated cardiac troponin I in the samples of individuals.

In some embodiments, the mass spectrometer used is TQ-ESI (electrospray with quadrupole) coupled to a reversed-phase chromatography column PFP. In some embodiments, the column coupled to the mass spectrometer can also be an immunoaffinity column linked to anti nitrated cardiac troponin I. In some embodiments, there may be two coupled columns. In some embodiments of the invention, other types of chromatographic columns may also be used.

The TQ-ESI mass spectrometer is a device able to monitor and quantify with high sensitivity and specificity one or more specific peptides and fragments thereof. In the first quadrupole the mass/charge ion ratio that one wishes to monitor is selected and the second quadrupole acts as a collision chamber where the ion selected in the first quadrupole is fragmented into several ions that are monitored and quantified in the third quadrupole.

In the TQ-ESI it is possible to simultaneously monitor and quantify the concentrations of nitrated cardiac troponin I and total cardiac troponin I.

In one embodiment, the chromatography coupled to a reverse-phase mass spectrometer with PFP resin provides for the separation of the peptide derived from the nitrated cardiac troponin I from the peptide derived from non-nitrated cardiac troponin I.

The $NO_2$ group present in the tyrosine peptide of nitrated cardiac troponin I has high affinity for PFP, and therefore this peptide has a longer column elution time when compared to the peptide of non-nitrated cardiac troponin I. In one embodiment of the invention, the concentrations of nitrated cardiac troponin I in samples of individuals is monitored by quantifying the tryptic fragment derived from nitrated cardiac troponin I AY($NO_2$)ATEPHAK (SEQ ID NO:2).

In some embodiments of the invention, the specific mass/charge (m/z) single charged ions and doubly charged ions of the peptide AY($NO_2$)ATEPHAK (SEQ ID NO: 2) are monitored. In this embodiment, ions derived from the fragmentation of the peptide AY($NO_2$)ATEPHAK (SEQ ID NO:2) in the collision chamber are also monitored. Quantified ions derived from AY($NO_2$)ATEPHAK (SEQ ID NO:2) fragmentation are: Y($NO_2$) single charge with specific mass/charge; AY($NO_2$) single charge with specific mass/charge; AY($NO_2$)A single charge with specific mass/charge and AY($NO_2$)ATE (SEQ ID NO:5) single charge with specific mass/charge.

In some embodiments, the ratio of derived from AY($NO_2$) ATEPHAK (SEQ ID NO:2) fragmentation is also monitored. The maintenance of the ions ratio derived from fragmentation of the peptide is an indication of diagnostic test specificity. The ion ratio must always be constant.

In some embodiments of the invention, in order to calculate the concentration of nitrated cardiac troponin I in the samples of individuals, the values obtained are compared with values from a standard curve of known concentrations. The readings of the standard curve values are always acquired parallel to the samples.

In some embodiments of the invention, a standard curve consists of the known concentrations of purified nitrated cardiac troponin I.

In some embodiments of the invention, a standard curve consists of the known concentrations of purified recombinant nitrated cardiac troponin I.

In some embodiments of the invention, a standard curve consists of the known concentrations of synthetic AY($NO_2$) ATEPHAK (SEQ ID NO:2) peptide.

In some embodiments of the invention an internal standard is used to correct the calculation of the concentration of nitrated cardiac troponin I in the sample. In some embodiments of the invention the internal standard is peptide AY($NO_2$)ATEPHAK (SEQ ID NO:2) of known concentration labeled with $^{13}C$ and $^{15}N$, inserted into each sample at the beginning of the process. In some embodiments of the invention the internal standard is nitrated cardiac troponin I nitrated of known concentration labeled with $^{13}C$ and $^{15}N$, inserted into each sample at the beginning of the process.

In some embodiments of the invention, the value of nitrated cardiac troponin I concentration in the sample will be used for the diagnosis of acute coronary syndrome. In some embodiments of the invention, the value of nitrated cardiac troponin I concentration in the sample will be used for the prognosis of acute coronary syndrome.

In some embodiments of the invention, the value of nitrated cardiac troponin I concentration in the sample will be used for determine the treatment of patients with acute coronary syndrome.

In some embodiments of the invention, the value of nitrated cardiac troponin I concentration in the sample will be used to monitor the treatment of patients with acute coronary syndrome.

In some embodiments of the invention, the value of nitrated cardiac troponin I concentration is proportional to the area affected by ischemia.

In some embodiments of the method, the ratio of nitrated cardiac troponin I and cardiac troponin I is used for the prognosis, diagnosis and management of patients with acute coronary syndrome.

In some embodiments, the concentrations of nitrated cardiac troponin I and total cardiac troponin I total are determined simultaneously, followed by calculating the concentrations ratio. In some embodiments these concentrations are determined by mass spectrometry coupled to liquid chromatography.

In this embodiment, the mass spectrometer used is TQ ESI (electrospray with quadrupole) coupled to a PFP reversed-phase chromatography column.

In some embodiments, the column coupled to the mass spectrometer can also be an immunoaffinity column linked to anti-nitrated cardiac troponin I. In some embodiments, there may be two coupled columns. In some embodiments of the method, other types of chromatographic columns can also be used.

In one embodiment of the invention the monitoring of the concentrations of nitrated cardiac troponin I and total cardiac troponin I present in subjects' samples is performed. In this embodiment the concentrations of AY(NO$_2$)ATEPHAK (SEQ ID NO:2) fragments derived of nitrated cardiac troponin I, and the AYATEPHAK (SEQ ID NO:3) fragment derived of cardiac troponin I are monitored and quantified.

In some embodiments of the invention, the monitoring of mono and doubly charged ions of specific mass/charge obtained from the peptide AY(NO$_2$)ATEPHAK (SEQ ID NO:2) and AYATEPHAK (SEQ ID NO:3) is performed.

In some embodiments of the invention, m/z specific single charged ions and m/z specific doubly charged ions from the peptide AY(NO$_2$)ATEPHAK (SEQ ID NO:2) are monitored. In one embodiment of the invention in question ions derived from fragmentation of the peptide in the collision chamber are also monitored. Ions derived from AY(NO$_2$)ATEPHAK (SEQ ID NO:2) fragmentation quantified are: Y(NO$_2$) single charge with specific mass/charge; AY(NO$_2$) single charge with specific mass/charge; AY(NO$_2$)A single charge with specific mass/charge and AY(NO$_2$)ATE (SEQ ID NO:5) single charge with specific mass/charge. Ions derived from AYATEPHAK (SEQ ID NO:3) fragmentation quantified are: ATEPHAK (SEQ ID NO:3) single charge with specific mass/charge; PHAK (SEQ ID NO:6) single charge with specific mass/charge; HAK single charge with specific mass/charge and AK single charge with specific mass/charge.

In some embodiments, the ions ratio monitoring is made from ions derived from AY(NO$_2$)ATEPHAK (SEQ ID NO:2) fragmentation and AYATEPHAK (SEQ ID NO:3) fragmentation. The maintenance of ions ratio derived from fragmentation of the peptides are a indicative of diagnostic test specificity. The ions ratio must be constant.

In some embodiments of the invention, for calculating the concentration of nitrated cardiac troponin I in the subjects' samples, the values are compared with values from a standard curve of known concentrations. The readings of the standard curve values are always acquired in parallel to the samples.

In some embodiments of the invention, a standard curve consists of the known concentrations of recombinant nitrated cardiac troponin I and recombinant non nitrated cardiac troponin I.

In some embodiments of the invention, a standard curve consists of the known concentrations of purified nitrated cardiac troponin I and purified non nitrated cardiac troponin.

In some embodiments of the invention, a standard curve consists of the known concentrations of synthetic AY(NO$_2$)ATEPHAK (SEQ ID NO:2) peptide and synthetic AYATEPHAK (SEQ ID NO:3) peptide.

In some embodiments of the invention an internal standard is used to correct the calculation of the concentration of nitrated cardiac troponin I and non nitrated cardiac troponin I in the sample. In some embodiments of the invention the internal standard is the peptide AY(NO$_2$)ATEPHAK (SEQ ID NO:2) and peptide AYATEPHAK (SEQ ID NO:3) of known concentration labeled with $^{13}$C and $^{15}$N, inserted into each sample at the beginning of the process.

In some embodiments of the invention the internal standard is nitrated cardiac troponin I to non-nitrated cardiac troponin I of known concentrations labeled with $^{13}$C and $^{15}$N, inserted into each sample at the beginning of the process.

In some embodiments of the invention, the ratio of nitrated cardiac troponin I and non-nitrated cardiac troponin I concentration will be used for the diagnosis of acute coronary syndrome.

In some embodiments of the invention, the ratio of nitrated cardiac troponin I to non-nitrated cardiac troponin concentration will be used for the prognosis of acute coronary syndrome.

In some embodiments of the invention, the ratio of nitrated cardiac troponin I to non-nitrated cardiac troponin concentration will be used for define patients treatment with acute coronary syndrome.

In some embodiments of the invention, the ratio of nitrated cardiac troponin I to non-nitrated cardiac troponin concentration will be used to monitor treatment of patients with acute coronary syndrome.

In some embodiments of the invention the ratio of nitrated cardiac troponin I to non-nitrated cardiac troponin concentration is proportional to the area affected by ischemia.

In some embodiments of the invention, the samples used may be plasma or serum.

In some embodiments of the invention, there is a first fractionation of the proteins present in the samples by chromatography. In some embodiments of the invention, the chromatography used is reverse phase. In some embodiments of the invention, the chromatography used is an immunoaffinity chromatography with monoclonal anti-nitrated cardiac troponin I linked to column. In some embodiments of the invention are used two sequential chromatographies. In some embodiments of the invention other types of chromatography columns can also be used.

In some embodiments of the invention, proteins are digested by trypsin after fractionation by chromatography. In some embodiments of the invention, proteins are digested prior to the chromatographic process.

Anti-Nitrated Cardiac Troponin I Antibody

The invention provides an antibody specific for nitrated cardiac troponin I. This antibody is specific for nitrated cardiac troponin I and show not affinity for nonnitrated cardiac troponin I or any other forms of post-translational modifications of cardiac troponin I other than nitration. The antibody does not recognize other isoforms of troponins not post translationally modified. The antibody does not recognize other isoforms of troponin post-translationally modified. The antibody does also does not recognize or detect other nitrated proteins other than the cardiac troponin I. The antibody does not cross-react with skeletal troponin.

The anti-nitrated cardiac troponin I is an antibody specific to a region comprising amino acids 16-35 of nitrated cardiac troponin I. This antibody recognizes the region that comprises the nitration of tyrosine, the nitration. The antibody was developed from the peptide PAPIRRRSSNY(NO$_2$)RAY(NO$_2$)ATEPHA (SEQ ID NO: 4).

In some embodiments of the invention, the antibody recognizes complete nitrated cardiac troponin I. In some embodiments of the invention, the antibody recognizes a peptide of nitrated cardiac troponin I AY(NO$_2$)ATHEPHAK (SEQ ID NO:2).

The antibody recognizes nitrated cardiac troponin I in humans, pigs, rats and mice. And due to homology of the protein, probably recognizes the nitrated cardiac troponin I in dog, cat, horse, orangutan, chimpanzee and possibly other animals.

In some embodiments of the invention, the antibody used is polyclonal anti-cardiac troponin I made in Hytest goat. In some embodiments of the invention the antibody used is polyclonal anti-nitrotyrosine made in Millipore rabbit. In some embodiments of the invention the antibody used is monoclonal anti-rabbit made in HRP-labeled mouse. In some embodiments of the invention the antibody used is anti-goat made in HRP-labeled mouse.

In some embodiments of the invention the antibody used is anti-rabbit made in Alexa 488-labeled mouse. In some embodiments of the invention the antibody used is anti-rabbit made in Alexa 555-labeled mouse. In some embodiments of the invention the antibody used is anti-goat made in Alexa-488 labeled mouse. In some embodiments of the invention the antibody used is anti-goat made in Alexa-555 labeled mouse.

Immunoassay Detection

Immunoassay techniques are based on antigen-antibody binding, thereby detection of the target molecule is made by using specific antibodies. The immunoassay techniques are characterized by generating rapid, sensitive, inexpensive and quantitative results.

The immunoassay techniques can be enzymatic such as ELISA and Western blot, fluorescent such as immunofluorescence and flow cytometry as or isotopic such as radioimmunoassay.

In some embodiments of the invention, nitrated cardiac troponin I may be detected and quantified by immunoassay. For development of immunoassay tests, we developed a monoclonal antibody made in mouse specific for nitrated cardiac troponin I.

In some embodiments of the invention, the immunoassay used was sandwich ELISA with monoclonal IgG anti-nitrated cardiac troponin I and secondary antibody anti-mouse IgG labeled with enzyme.

In some embodiments of the invention, the immunoassay used was ELISA by competition, using the monoclonal antibody IgG anti-nitrated cardiac troponin I and secondary antibody anti-mouse IgG labeled with enzyme. In this embodiment of method peptide AY(NO$_2$)ATEPHAK (SEQ ID NO:2) was used as a competitor. In some embodiments of the invention the competitive peptide is synthetic.

In some embodiments of the invention, in order to calculate the concentration of nitrated cardiac troponin I in the subjects' samples, the values are compared with values from a standard curve of known concentrations. The readings of the standard curve values are always acquired parallel to the samples.

In some embodiments of the invention, a standard curve consists of known growing concentrations of recombinant nitrated cardiac troponin I.

In some embodiments of the invention, a standard curve consists of known growing concentrations of purified nitrated cardiac troponin I.

In some embodiments of the invention, a standard curve consists of known growing concentrations of synthetic AY(NO$_2$)ATEPHAK (SEQ ID NO:2) peptide.

In some embodiments of the invention, the value of nitrated cardiac troponin I concentration will be used for the diagnosis of acute coronary syndrome.

In some embodiments of the invention, the value of nitrated cardiac troponin I concentration will be used for the prognosis of acute coronary syndrome.

In some embodiments of the invention, the value of nitrated cardiac troponin I concentration will be used to define treatment for patients with acute coronary syndrome.

In some embodiments of the invention, the value of nitrated cardiac troponin I concentration will be used to monitor treatment of patients with acute coronary syndrome.

In some embodiments of the invention, the value of nitrated cardiac troponin I concentration is proportional to the area affected by ischemia.

Nitrated cardiac troponin I was characterized by detection of peptide fragments by mass spectrometry ESI-TQ coupled to liquid chromatography. These features provide a method of determining the presence and concentration of molecules in biological samples.

Nitrated cardiac troponin I was also characterized by immunoassay with monoclonal antibody specific for nitrated cardiac troponin I. This method is also used to determine the concentrations of cardiac troponin I nitrated samples of individuals.

This biomarker was discovered by immunoprecipitation of all nitrated proteins present in the serum followed by detection of nitrated cardiac troponin I by Western blot.

The discovery of biomarker, first used pigs as models. We performed myocardial ischemia induced by balloon catheter occlusion for 10 minutes followed by reperfusion or not.

Serum samples were collected from these animals immediately before the occlusion, immediately after reperfusion and at intervals of 30 minutes after the onset of reperfusion for up to 3 hours.

Serum samples were incubated with beads attached to protein A (Invitrogen DynalBeads) coupled to polyclonal antibodies made in rabbit anti-nitrotyrosine (Millipore).

The immunoprecipitates proteins were eluted of antibodies and applied in gel 12% SDS-PAGE, transferred to PVDF membrane (GE) and incubated with detection monoclonal antibody made in mouse anti-nitrated cardiac troponin I or polyclonal antibody made in goat anti-cardiac troponin I. Serum samples controls, ie, before induction of ischemia, there is the detection of nitrated cardiac troponin I. Serum samples collected after ischemia induction for the detection of nitrated cardiac troponin I. This method is described in more detail in the examples section.

EXAMPLES

Example 1

Identification of Nitrated Cardiac Troponin I as a Biomarker for Myocardial Ischemia and Acute Coronary Disease In order to identify nitrated cardiac troponin I, an enrichment of nitrated serum proteins was performed followed by the identification of cardiac troponin I by western blot.

The enrichment of nitrated serum proteins was performed by immunoprecipitation according to a modified protocol as described by Parastatidis, 2007.

Protein A magnetic beads (Invitrogen Dynalbeads) were washed three times with PBS and then incubated with anti-nitrotyrosine antibody (Millipore) at a ratio of 1 µg of antibody for each 5 µL of protein A magnetic beads. The antibody was diluted in PBS in the same final volume used for the protein A magnetic beads. The beads and antibodies were stirred at 4° C. for 16 hours. After incubation, the supernatant was discarded and the bead-antibody complex was washed with 0.1% PBST three times with agitation for five minutes. To perform the covalent bond between the antibody and protein A coupled to the bead, the complex was incubated with 6.5 mg/mL of DMP diluted in 200 mM triethanolamine for 30 minutes under stirring at room temperature.

This process was repeated three times, intercalated with a washing with 200 mM triethanolamine with stirring for five minutes between incubations with DMP. After the linking, the quenching was performed with two five-minute incubations with 50 mM ethanolamine. To remove the antibodies that are not covalently linked, the bead-antibody complex was incubated twice for 10 minutes at pH 2.5 with 1M glycine. The bead-antibody complex was stored at 4° C. in PBS with 2 mM sodium azide. For the identification of nitrated cardiac troponin I, serum and heart tissue of animal model myocardial ischemia was used.

The total protein was measured by the method of Bradford (BioRad). 10 mg of protein were separated and pre-incubated with 50 µL of magnetic beads coupled to protein A (Invitrogen Dynalbeads) under stirring at 4° C. for 16 hours. Then, the supernatant was removed and incubated with 50 µL of protein A magnetic beads covalently linked to the antibodies under agitation at 4° C. for 16 hours. After incubation, the supernatant was discarded and the beads were washed three times with PBST 0.1%. The nitrated proteins were eluted with three consecutive washes of 100 mL of 0.1 M glycine pH 2.5. The pH of the solution containing the protein was nitrated balanced with 25 uL of 1M Tris-HCl pH 9.0. They were then dried by speed-vac. To confirm the enrichment of nitrated serum proteins, immunoprecipitated protein was loaded on 12% SDS-PAGE, followed by silver staining (Sigma) (FIG. 1).

Protein immunoprecipitates were quantified using a ND-1000 spectrophotometer nanodrop (Thermo Scientific) at a wavelength of 280 nm. A nitrated BSA standard curve was used for calculating the protein concentrations.

A 15% SDS-PAGE gel electrophoresis, was performed using 5 µg of nitrated 15% SDS-PAGE immunoprecipitates. Protein samples were inserted in parallel lanes into the gel together with a molecular weight marker (Kaleidoscope BioRad). After the migration of proteins in the gel, the proteins were transferred to a PVDF membrane (GE HybondP) on the semi-dry for 50 minutes. After the transfer, the membrane remained for 16 hours at 37° C. for perfect drying. The next day the membrane was blocked for 1 hour with 5% milk powder diluted in 0.1% PBST. After 3 washes with 0.1% PBST, the membrane was incubated for 16 hours at 4° C. under stirring with a polyclonal goat anti-cardiac troponin I antibody (commercially obtained from Hytest #4T21) diluted in 5% milk powder diluted in PBST 0.1%. After washing, the membrane was incubated for 1 hour with rabbit anti-goat IgG antibody conjugated to HRP, washed again and revealed by the ECL method.

Using immunoenrichment and immunodetection techniques it was possible to detremine that cardiac troponin I is nitrated after myocardial ischemia. Furthermore, it is possible to detect said nitrated cardiac troponin I in the serum of individuals after the ischemic event. Accordingly. Nitrated cardiac troponin I may be used as a biomarker for cardiac ischemia.

Example 2

Figure 3:
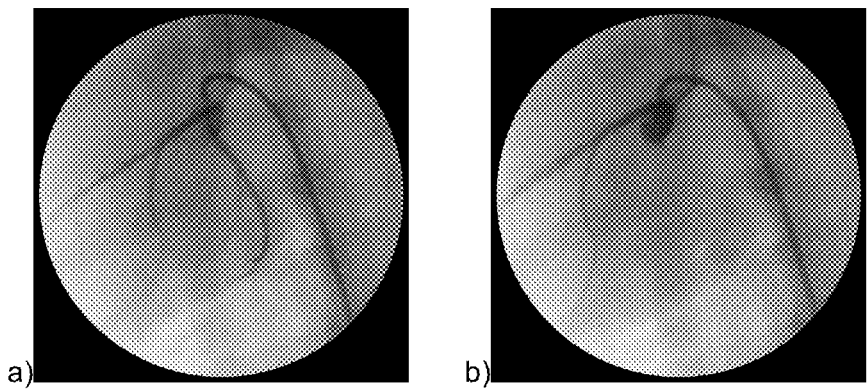
FIG. 3 shows a Left circumflex coronary artery angiography a) pre-occlusion and b) post-occlusion.

Identification of Nitrated Cardiac Troponin I in Porcine Models of Controlled-Ischemia Three pigs were subjected to controlled-ischemia in the proximal left circumflex coronary artery by an occlusion for 10 minutes using a balloon-catheter, followed by 3 hours of reperfusion (FIG. 3). 5 mL samples of serum were collected before the intervention, immediately after the intervention and at 10, 30, 60, 90, 120 and 180 minutes after reperfusion in order to analyze the concentrations of CK-MB, troponin I and ultra-sensitive Troponin T. These proteins are markers of tissue necrosis, which occurs with an occlusion of longer than 30 minutes and would be circulating after approximately 6 hours of the ischemic event with the onset of necrosis.

Figure 4:
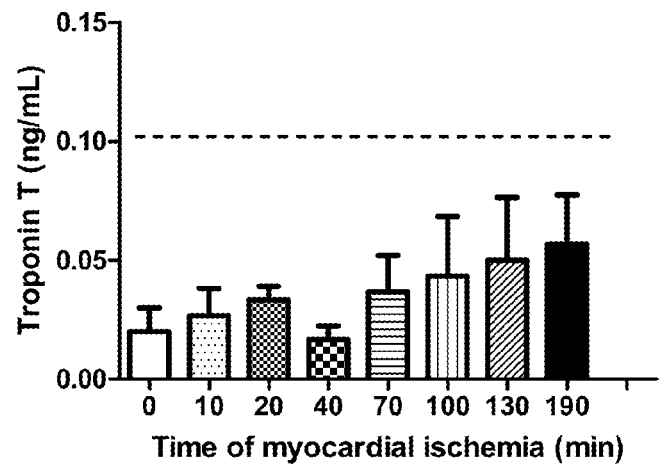
FIG. 4 shows the dosage of cardiac necrosis markers. A) average concentrations of circulating troponin T in ischemic animals; B) average concentrations of circulating CK; C) average ultrasensitive troponin T measurements of ischemic animals. The dotted lines indicate the reference values (Troponin T: 0.1 ng/mL, CK: 5 ng/mL, ultrasensitive troponin T: 0.014 ng/mL).
Figure 4:
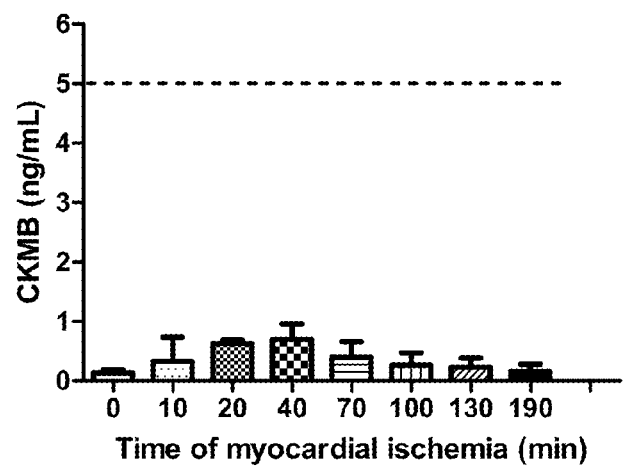
Figure 4:
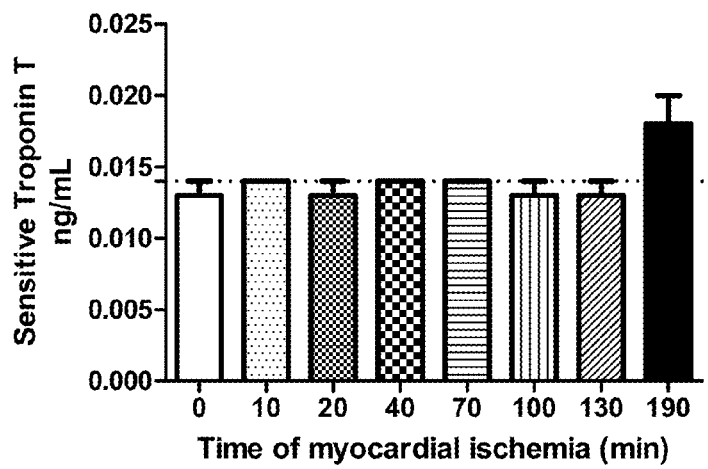

As expected, no increase of CK-MB, troponin T and ultra-sensitive Troponin T in the serum of the animals was observed, except for one animal during the last collection point which was responsible for an increase in the mean values observed (FIG. 4).

Figure 5:
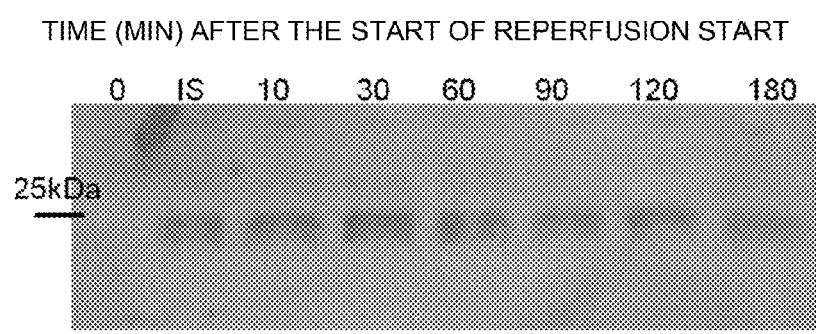
FIG. 5 shows a Western blot detecting nitrated cardiac troponin I (25 kDa) in a pig serum sample collected after heart ischemia and reperfusion. O—Prior to the induction of ischemia, IS—Immediately after reperfusion, 10, 30, 60, 90, 120, 180-minutes after reperfusion.

The enrichment of the nitrated portion of biological samples was performed by immunoprecipitation. Protein A magnetic beads were covalently linked to anti-nitrotyrosine polyclonal antibody (1:5 ratio). Subsequently, the complex was incubated with 10 mg of serum or plasma proteins from. The complex was washed and the proteins bound to the antibody were eluted with 800 mm acetic acid. Then the sample was quantified and 5 µg of protein were applied to 12% SDS-PAGE electrophoresis. Proteins were transferred to membrane and incubated with a polyclonal anti-cardiac troponin I and revealed by ECL (FIG. 5).

The results demonstrated that before the induction of ischemia, the presence of nitrated cardiac troponin I in the serum of the animal could not be observed. The protein could be identified immediately after ischemia and remained in the blood circulation for up to 3 hours after the induction of ischemia.

Example 3

Identification of Nitrated Cardiac Troponin I in Porcine Models of Acute Myocardial Infarction.

Figure 6:
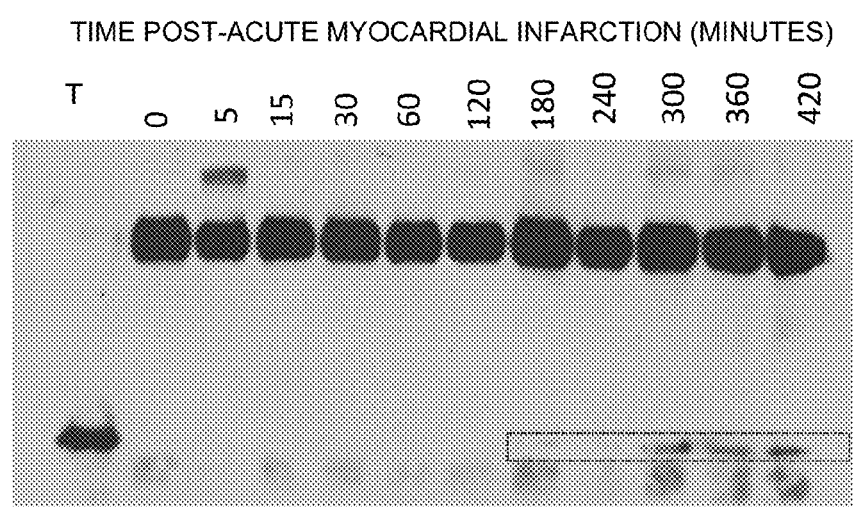
FIG. 6 shows a Western blot detecting nitrated cardiac troponin I (25 kDa) in a pig serum sample after acute myocardial infarction. purified T—cardiac troponin I, 0—Before the ischemia induction, 5, 15, 30, 60, 120, 180, 240, 300, 360, 420—minutes after acute myocardial infarction. The highlighted area indicates the samples with positive results.

Five pigs were subjected to a permanent occlusion of the circumflex coronary artery using a polystyrene graft. 5 mL samples of serum were collected before the intervention, immediately after the intervention and at 10, 30, 60, 90, 120 and 180 minutes after reperfusion in order to analyze the concentrations of CK-MB, troponin I and ultra-sensitive Troponin T. These proteins are markers of tissue necrosis, which occurs with an occlusion of longer than 30 minutes and would be circulating after approximately 6 hours of the ischemic event with the onset of necrosis. As expected, troponin T increased after 6 hours of onset of acute myocardial infarction. Ultra-sensitive troponin T rose early after onset of ischemia without reperfusion. Protein A magnetic beads were covalently linked to anti-nitrotyrosine polyclonal antibody (1:5 ratio). Subsequently, the complex was incubated with 10 mg of serum or plasma proteins from. The complex was washed and the proteins bound to the antibody were eluted with 800 mm acetic acid. Then, the sample was quantified and 5 µg of protein were applied to 12% SDS-PAGE electrophoresis. Proteins were transferred to membrane and incubated with a polyclonal anti-cardiac troponin I and revealed by ECL (FIG. 6).

The results demonstrate that in situations where there is no reperfusion, nitrated cardiac troponin I is detected in the serum after approximately 180 minutes of the onset of acute myocardial infarction.

Example 4

Identification of Nitrated Cardiac Troponin I in Patients after Angioplasty with Pharmacological Stent Therapy.

Patients with stable angina were subjected to angioplasty with conventional stent implantation, "Hospital das Clinicas—Instituto do Coração" from the Faculty of Medicine at the University of Sao Paulo were enrolled in this prospective study of ischemia markers. The protocol was submitted for approval by the Committee of Ethics in Research of the "Hospital das Clínicas"—University of Sao Paulo. Five patients with stable angina and an indication of angioplasty with stent implantation were eligible for the study. These patients had documented ischemia on continuous electrocardiographic monitoring during the angiographic procedure: fleeting and transient elevation of the ST segment. Serum samples were collected before the procedure, immediately after and every 30 minutes until completion of 3 hours of induced ischemia.

Figure 7:
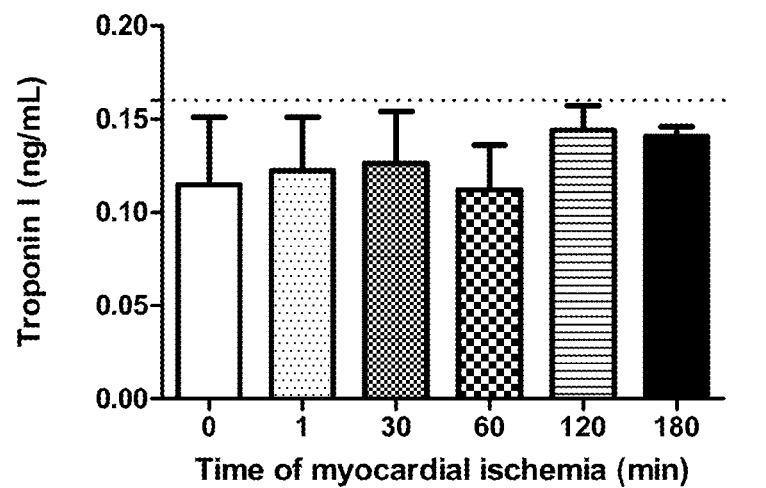
FIG. 7 shows the dosage of circulating markers of cardiac necrosis in patients after ischemia induction by stent implant. A) Average of troponin I. B) Average ultra-sensitive Troponin T. The dotted lines indicate the reference values (Troponin I: 0.160 ng/mL, ultrasensitive troponin T: 0.014 ng/mL).
Figure 7:
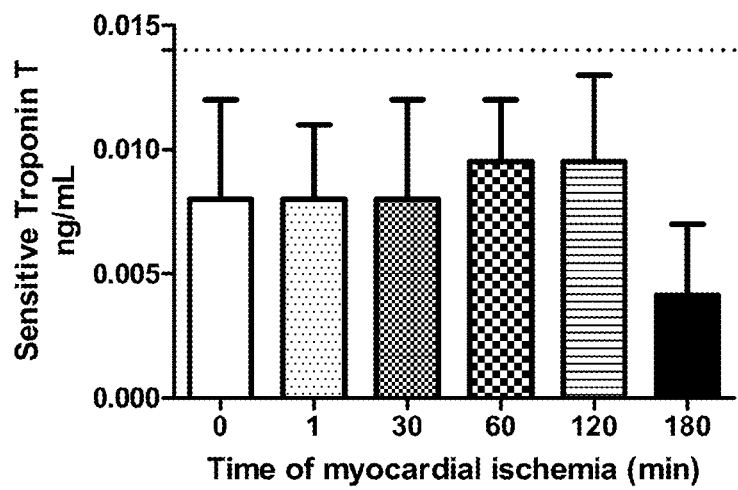

Ultra-sensitive troponin I and troponin T in patient's serum were dosed, and as expected there was no increase in these markers (FIG. 7).

Figure 8:
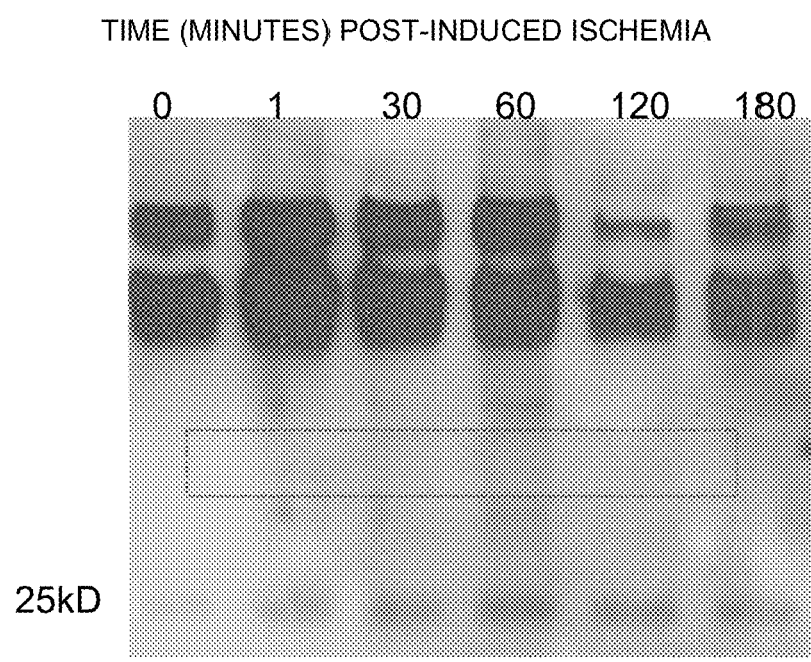
FIG. 8 shows a Western blot detection of nitrated cardiac troponin I (25 kDa) in patient serum sample after induced ischemia. Time O— Before the ischemia induction; Times 1, 30, 60, 120, 180 minutes after ischemia. The highlighted area indicates the samples with positive results. The results demonstrate that, in patients with angina, prior to the induction ischemia, it was not possible to detect nitrated cardiac troponin I in the serum. The protein was identified after the induction of ischemia and remained in the serum up to 3 hours from the ischemic event.

The protein A magnetic beads (Invitrogen) were covalently linked to the anti-nitrotyrosine polyclonal antibody (Millipore) and the complex was incubated with 10 mg of proteins from serum or plasma. The complex was washed and the bound proteins were eluted with 800 mM acetic acid. Subsequently, the sample was quantified and 5 μg of protein sample was applied to an 12% SDS-PAGE electrophoresis gel. The proteins were transferred to a membrane and incubated with a polyclonal anti-cardiac troponin I and revealed by the ECL method (FIG. 8).

Example 5

Identification of Nitrated Cardiac Troponin I in a Cellular Model of Cardiac Ischemia In Vitro Immunofluorescence reactions were performed in cardiomyocytes after ischemia in vitro in order to verify the possible co-localization of the markings of the anti-cardiac troponin I and anti-nitrotyrosine antibodies.

In vitro ischemia was developed by placing cultured cardiomyocytes under low oxygen tension, low glucose and acidic pH. A time curve was prepared at intervals of 15, 30 and 60 minutes of ischemia followed by 60 minutes of reperfusion with normal oxygen tension to determine the best point for ischemia. Sixty minutes were chosen as an experimental point, when a stronger staining of the anti-nitrotyrosine antibody was obtained.

Figure 9:
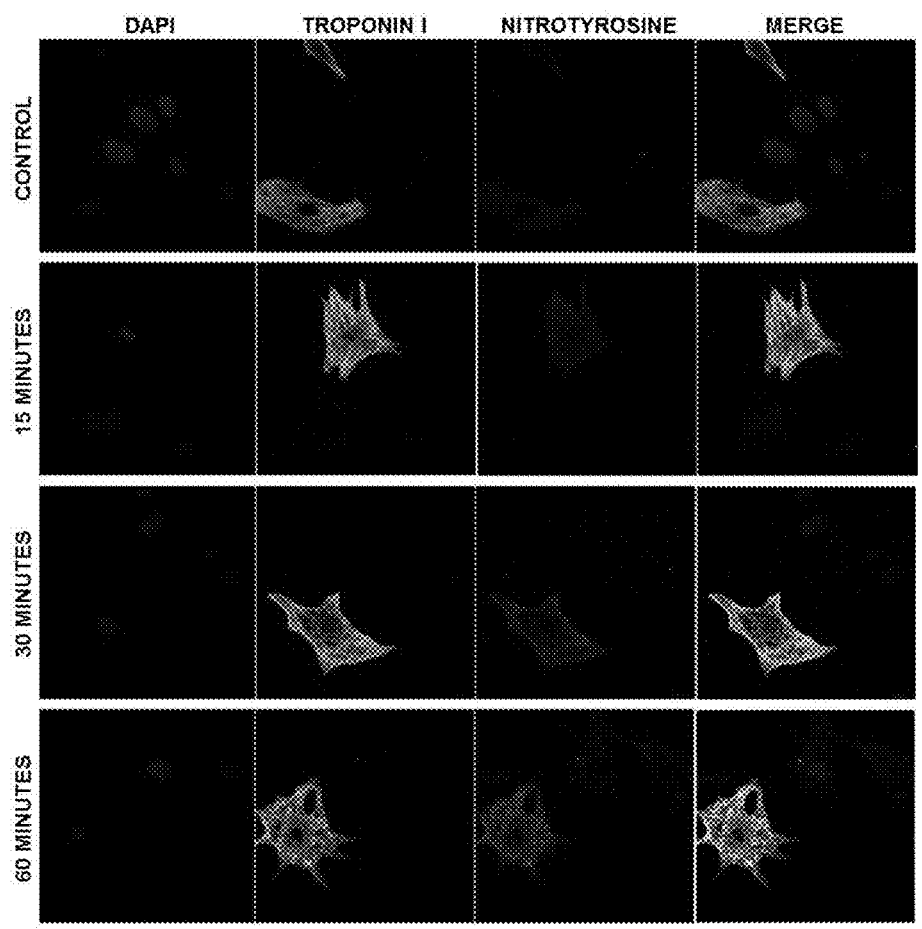
FIG. 9 shows the co-localization of cardiac troponin I and nitrotyrosine by immunofluorescence in ischemic cardiomyocyte culture. In labeling of the nuclei (DAPI), marking cardiac troponin I, marking nitrotyrosine and in merge overlapping of the markings. Left: indication of the ischemia time in minutes. Photos taken in confocal. Magnification of 63×.

The marking for the anti-cardiac troponin I antibody co-localized with the marking for the anti-nitrotyrosine antibody (FIG. 9). Cells that did not undergo ischemia showed a weak labeling of nitrotyrosine compared to ischemic cells. Cultures that underwent in vitro ischemia presented a stronger co-localization, suggesting that cardiac troponin I is nitrated during ischemia.

Example 6

Figure 10:
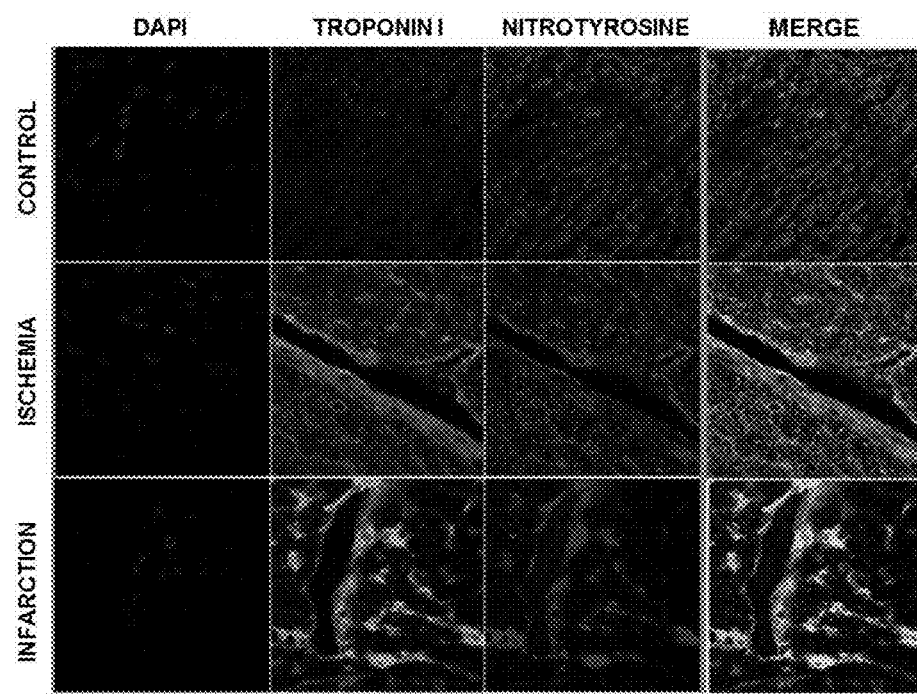
FIG. 10 shows the marking of cardiac troponin I and nitrotyrosine by immunofluorescence in cardiac tissue of animal models. In blue labeling of the nuclei (DAPI), green marking cardiac troponin I, red marking nitrotyrosine and in merge overlapping of the markings Left: indication of the control animal, myocardial ischemia animal and myocardial infarction animal. Photos taken in confocal. Magnification of 63×.
Figure 11:
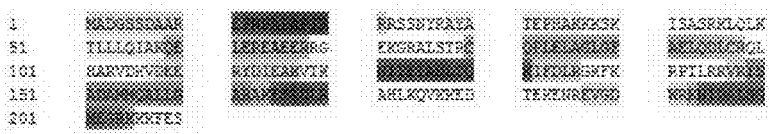
FIG. 11 shows the digestion of nitrated cardiac troponin I by trypsin.
Figure 12:
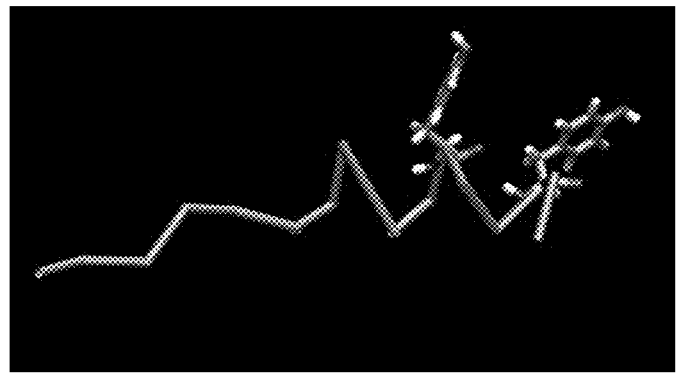
FIG. 12 shows the structure of peptide PAPIRRRSSNY(NO$_2$)RAY(NO$_2$)ATEPHA (SEQ ID NO:4) used for in the development of the anti-nitrated cardiac troponin I antibody. A nitrated tyrosine residue in is evidenced in the structure.
Figure 13:
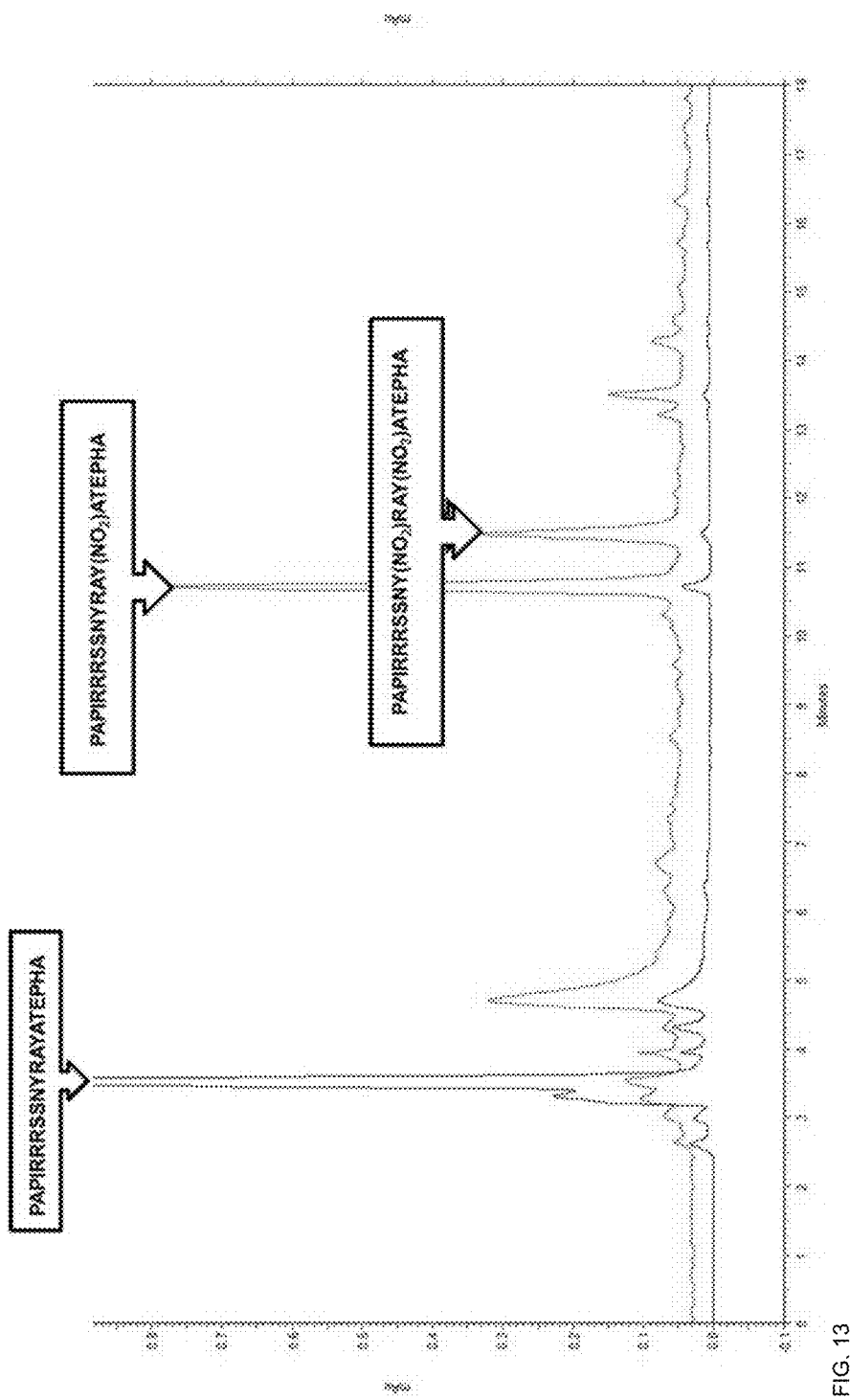
FIG. 13 shows a chromatogram of nitrated PAPIRRRSSNY(NO$_2$)RAY(NO$_2$)ATEPHA (SEQ ID NO:4) peptide purification by HPLC.

Identification of Nitrated Cardiac Troponin I in the Myocardium of Murine Model of Cardiac Ischemia and Acute Myocardial Infarction In order to reproduce the nitration of troponin I in vitro, we performed ischemia and infarction in rats. The hearts of three rats in each group (control, 10 minutes ischemia and infarction) were frozen. Histological fresh slides were prepared and subsequent immunofluorescence assay with anti-troponin I and anti-nitrotyrosine antibodies was performed. The data reproduce the results found in in vitro ischemia, showing that the nitration of cardiac troponin I also occurs in vivo (FIG. 10). The data suggest that the greater the time of low oxygen tension in the cardiac muscle, the greater the amount of nitrated troponin I.

Example 7

Molecular Characterization of Nitrated Cardiac Troponin I

In order to characterize and describe the nitration of cardiac troponin I, a purified human cardiac troponin I was nitrated in vitro and analyzed by tandem mass spectrometry coupled to liquid chromatography.

For the in vitro nitration assay we used human cardiac troponin I (Sigma #T9924). Peroxynitrite was synthesized and subsequently 40 μg of cardiac troponin I were nitrated with 1 mM peroxynitrite.

The nitrated protein was trypsin digested for 16 hours at 37° C. and the peptides were analyzed on a LC-ESI-Q-TOF (Synapt II-Waters). The analysis of mass spectrometry permited the identification and characterization of the nitrated peptide and the site of nitration (tyrosine 29). The analysis covered 66.7% of the protein, including the site of nitration.

The nitrated cardiac troponin I sequence is (SEQ ID NO:1):

MADGSSDAAREPRPAPAPIRRRSSNY(NO$_2$)RAY(NO$_2$)ATEPHAKKKS

KISASRKLQLKTLLLQIAKQELEREAEERRGEKGRALSTRCQPLELAGL

GFAELQDLCRQLHARVDKVDEERYDIEAKVTKNITEIADLTQKIFDLRG

KFKRPTLRRVRISADAMMQALLGARAKESLDLRAHLKQVKKEDTEKENR

EVGDWRKNIDALSGMEGRKKKFESL

The nitration can occur in one or two tyrosines. The same results were obtained for troponin purified from human samples.

Example 8

Analysis of Nitrated Cardiac Troponin I in Human Samples by LC-ESI-TQS

For the identification and quantification of nitrated cardiac troponin I in patient samples a LC-ESI-TQS mass spectrometer was used (Xevo TQ-S-Waters). The test was optimized using the peptides AY(NO$_2$)ATEPHAK (SEQ ID NO:2) derived from nitrated cardiac troponin I, and AYATEPHAK (SEQ ID NO:3) derived from non-nitrated cardiac troponin I.

The peptides were synthesized to a purity greater than 90%, nitrated with 2 mM of peroxynitrite and then purified by HPLC.

The mass spectrometer was coupled to a chromatography column type PFP, which allowed for a differential binding and elution of the nitrated and non-nitrated cardiac troponin I peptides.

The monitoring of m/z specific single and doubly charged ions was performed using peptide AY(NO$_2$)ATEPHAK (SEQ ID NO:2). The ions derived from the fragmentation of the peptide in the collision chamber was also monitored.

Quantified ions derived from AY(NO$_2$)ATEPHAK (SEQ ID NO:2) fragmentation are: Y(NO$_2$) single charge with specific mass/charge; AY(NO$_2$) single charge with specific mass/charge; AY(NO$_2$)A single charge with specific mass/charge and AY(NO$_2$)ATE (SEQ ID NO:5) single charge with specific mass/charge.

Quantified ions derived from AYATEPHAK (SEQ ID NO:3) fragmentation quantified are: ATEPHAK (SEQ ID NO:7) single charge with specific mass/charge; PHAK (SEQ ID NO:6) single charge with specific mass/charge; HAK single charge with specific mass/charge and AK single charge with specific mass/charge.

After the standardization of parameters, nitrated cardiac troponin I could be identified and quantified in serum, plasma, proteins, immunoprecipitated protein and tissue protein. 50 μL of sample (serum, immunoprecipitated protein or tissue) was aliquoted with 10 μL NH$_4$HCO$_3$ solution. 25 μL of 0.2% RapiGest SF (Waters) were added. The solution was subjected to vortex and incubated for 15 minutes at 80° C. After incubation, the solution was left to cool to room temperature and 2.5 mL of 100 mM DTT were added. The solution was incubated for 30 min at 60° C. and 2.5 mL of 300 mM Iodoacetoamide were added. The reaction was incubated for 30 minutes in the dark at room temperature. After alkylation, 10 µL of 0.05 g/uL trypsin (Promega) diluted in 50 mM $NH_4HCO_3$ were added. The solution was subjected to vortex and incubated for 16 hours at 37° C.

After the trypsin digestion to hydrolyze the RapiGest, 10 µL of 5% TFA (Pierce) were added to the solution which was incubated for 90 min at 37° C. Subsequently, the samples were centrifuged at 14000 rpm for 30 minutes at 6° C.

The samples were analyzed in the spectrometer using a curve for nitrated cardiac troponin I concentrations in parallel. An internal standard was used to correct the calculation of the concentration of nitrated and non-nitrated cardiac troponin I in the sample. The internal standards are peptide $AY(NO_2)ATEPHAK$ (SEQ ID NO:2) and peptide AYATEPHAK (SEQ ID NO:3) of known concentration labeled with $^{13}C$ and $^{15}N$ and inserted into each sample at the beginning of the process.

Example 9

Anti-Nitrated Cardiac Troponin I Antibody

Based on the analysis of the sequence and structure of the nitrated cardiac troponin I peptides, the peptide PAPIRRRSSNY($NO_2$)RAY($NO_2$)ATEPHA (SEQ ID NO:4) was chosen. This peptide was chosen because it presents two sites of tyrosine nitration. This peptide is also exposed in the 3D structure of nitrated cardiac troponin I. This peptide corresponds to the region comprising amino acids 16-35 of nitrated cardiac troponin I.

a) Peptide Synthesis.

15 mg of peptide PAPIRRRSSNY($NO_2$)RAY($NO_2$)ATEPHA (SEQ ID NO:4) were synthesized to >90% purity. The peptide was nitrated with 2 mM of peroxynitrite, followed by C18 column HPLC purification. The purified nitrated peptide was used in the conjugation and immunization assays.

b) Immunization and ELISA Screening.

The modified peptide was conjugated to a carrier protein, such as KLH or BSA.

Balb/c mice are immunized and boosted with a standard immunization protocol. Tail bleedings were screened by ELISA with nitrated and non-nitrated peptides, and nitrated BSA.

c) Fusion and Screening.

Two fusions (1-2 spleens per fusion) were performed on the mice that responded better to the nitro-peptide in phase b). The hybridoma cells were expanded and screened by ELISA with nitro and non-nitro peptides, and nitrated BSA. All positive clones was expanded into 24-well plates. The clones with the best ELISA values and specificity to nitrated-peptide was selected for subcloning.

d) Subcloning, Expansion and Cryopreservation.

Hybridoma subclones was screened by ELISA with nitrated and non-nitrated-peptide. Up to five positive parental clones were sub-cloned by limiting dilution, isotyping the final positive supernatants. Two subclones for each parental clone were and expanded and cryopreserved.

REFERENCES

Abello N, Kerstjens H A, Postma D S, Bischoff R. Protein tyrosine nitration: selectivity, physicochemical and biological consequences, denitration, and proteomics methods for the identification of tyrosine-nitrated proteins. J Proteome Res. 2009 July; 8(7):3222-38.

Ahmed N, Babaei-Jadidi R, Howell S K, Beisswenger P J, Thornalley P J. Degradation products of proteins damaged by glycation, oxidation and nitration in clinical type 1 diabetes. Diabetologia. 2005 August; 48(8):1590-603.

Aslan M, Dogan S. Proteomic detection of nitroproteins as potential biomarkers for cardiovascular disease. J. Proteomics. 2011 May 27.

Bhaysar P K, Brand N J, Yacoub M H, Barton P J. Isolation and characterization of the human cardiac troponin I gene (TNNI3). Genomics. 1996 Jul. 1; 35(1):11-23.

Castegna A, Thongboonkerd V, Klein J B, Lynn B, Markesbery W R, Butterfield D A. Proteomic identification of nitrated proteins in Alzheimer's disease brain. J. Neurochem. 2003 June; 85(6):1394-401.

Choi D Y, Zhang J, Bing G. Aging enhances the neuroinflammatory response and alpha-synuclein nitration in rats. Neurobiol Aging. 2010 September; 31(9):1649-53.

Debashis R et al. Ischemia-Modified Albumin Concentrations in Patients with Peripheral Vascular Disease and Exercise-Induced Skeletal Muscle Ischemia. Clinical Chemistry 50, No. 9, 2004

Eggers K M, Jaffe A S, Lind L, Venge P, Lindahl B. Value of cardiac troponin I cutoff concentrations below the 99th percentile for clinical decision-making Clin Chem. 2009 January; 55(1):85-92.

Gole M D, Souza J M, Choi I, Hertkorn C, Malcolm S, Foust R F, 3rd, et al. Plasma proteins modified by tyrosine nitration in acute respiratory distress syndrome. Am J Physiol Lung Cell Mol. Physiol. 2000 May; 278(5):L961-7.

Heffron S P, Parastatidis I, Cuchel M, Wolfe M L, Tadesse M G, Mohler E R, 3rd, et al. Inflammation induces fibrinogen nitration in experimental human endotoxemia. Free Radic Biol Med. 2009 Oct. 15; 47(8):1140-6.

Hochholzer W, Reichlin T, Twerenbold R, Stelzig C, Hochholzer K, Meissner J, et al. Incremental Value of High-Sensitivity Cardiac Troponin T for Risk Prediction in Patients with Suspected Acute Myocardial Infarction. Clin Chem. 2011 Jul. 19.

Isobe C, Abe T, Terayama Y. Remarkable increase in 3-nitrotyrosine in the cerebrospinal fluid in patients with lacunar stroke. Brain Res. 2009 Dec. 11; 1305:132-6.

Levrand S, Vannay-Bouchiche C, Pesse B, Pacher P, Feihl F, Waeber B, et al. Peroxynitrite is a major trigger of cardiomyocyte apoptosis in vitro and in vivo. Free Radic Biol Med. 2006 Sep. 15; 41(6):886-95.

Lippi, Giuseppe; Brocco, Giorgio; Salvagno, Gian Luca; Montagnana, Martina; Dima, Francesco; Guidi, Gian Cesare High-workload endurance training may increase serum ischemia-modified albumin concentrations. Clinical Chemistry & Laboratory Medicine. 43(7):741-744, July 2005.

Lloyd-Jones D, Adams R, Carnethon M, De Simone G, Ferguson T B, Flegal K, et al. Heart disease and stroke statistics—2009 update: a report from the American Heart Association Statistics Committee and Stroke Statistics Subcommittee. Circulation. 2009 Jan. 27; 119(3):e21-181

Masson S, Latini R, Anand I S. An update on cardiac troponins as circulating biomarkers in heart failure. Curr Heart Fail Rep. 2010 March; 7(1):15-21.

McCaig L F, Burt C W. National Hospital Ambulatory Medical Care Survey: 2002 Emergency Department summary. Advance data from Vital and Health Statistics. Hyattsville, Md.: National Center for Health Statistics; 2004.

Morrow D A, Cannon C P, Jesse R L, Newby L K, Ravkilde J, Storrow A B, et al. National Academy of Clinical Biochemistry Laboratory Medicine Practice Guidelines: Clinical characteristics and utilization of biochemical markers in acute coronary syndromes. Circulation. 2007 Apr. 3; 115(13):e356-75.

Parastatidis I, Thomson L, Fries D M, Moore R E, Tohyama J, Fu X, et al. Increased protein nitration burden in the atherosclerotic lesions and plasma of apolipoprotein A-I deficient mice. Circ Res. 2007 Aug. 17; 101(4):368-76.

Parikh S V, de Lemos J A. Biomarkers in cardiovascular disease: integrating pathophysiology into clinical practice. Am J Med. Sci. 2006 October; 332(4):186-97

Peluffo G, Radi R. Biochemistry of protein tyrosine nitration in cardiovascular pathology. Cardiovasc Res. 2007 Jul. 15; 75(2):291-302.

Piroddi M, Palmese A, Pilolli F, Amoresano A, Pucci P, Ronco C, et al. Plasma nitroproteome of kidney disease patients. Amino Acids. 2011 February; 40(2):653-67.

Pope J H, Aufderheide T P, Ruthazer R, Woolard R H, Feldman J A, Beshansky J R, et al. Missed diagnoses of acute cardiac ischemia in the emergency department. N Engl J Med 2000; 342(16):1163-70

Reichlin T, Hochholzer W, Bassetti S, Steuer S, Stelzig C, Hartwiger S, et al. Early diagnosis of myocardial infarction with sensitive cardiac troponin assays. N Engl J. Med. 2009 Aug. 27; 361(9):858-67.

Singh V, Martinezclark P, Pascual M, Shaw E S, O'Neill W W. Cardiac biomarkers—the old and the new: a review. Coron Artery Dis. 2010 June; 21(4):244-56.

Turko I V, Li L, Aulak K S, Stuehr D J, Chang J Y, Murad F. Protein tyrosine nitration in the mitochondria from diabetic mouse heart. Implications to dysfunctional mitochondria in diabetes. J Biol. Chem. 2003 Sep. 5; 278(36): 33972-7.

Tyther R, McDonagh B, Sheehan D. Proteomics in investigation of protein nitration in kidney disease: technical challenges and perspectives from the spontaneously hypertensive rat. Mass Spectrom Rev. 2011 January-February; 30(1):121-41.

The invention claimed is:

1. A method comprising:

(a) providing a plasma or serum sample from a human subject who has or is suspected of having cardiac disease;

(b) incubating the sample with an antibody suitable for capturing nitrated cardiac troponin I;

(c) detecting immunocaptured nitrated cardiac troponin I obtained in step (b) by mass spectrometer or immunoassay (d) measuring the level of non-nitrated cardiac troponin I in the plasma or serum sample;

(e) determining a ratio of non-nitrated cardiac troponin I to nitrated cardiac troponin I present in said sample; and (f) comparing said ratio with reference values obtained from patients with cardiac ischemia.

2. The method of claim 1, which further comprises comparing a concentration of nitrated cardiac troponin I in the sample with a standard curve.

3. The method of claim 1 which further comprises comparing a concentration of nitrated cardiac troponin I with reference values obtained from patients with acute coronary syndrome.

4. The method of claim 1, wherein the step of detecting comprises measuring with a mass spectrometer.

5. The method of claim 1, wherein the step of detecting comprises enzymatically digesting proteins followed by liquid chromatography and tandem mass spectrometry.

6. The method of claim 1, wherein the cardiac disease is acute cardiac ischemia or cardiac ischemia due to chronic coronary artery disease.

7. The method of claim 1, further comprising treating the subject for myocardial ischemia.

8. The method of claim 1, further comprising monitoring treatment of the subject for myocardial ischemia.

9. The method of claim 1 wherein the step of detecting comprises immunoassay.

10. A method comprising:
    (a) providing a plasma or serum sample from a human subject who has or is suspected of having cardiac disease;
    (b) incubating the sample with an antibody suitable for capturing nitrated cardiac troponin I;
    (c) detecting immunocaptured nitrated cardiac troponin I obtained in step (b) by mass spectrometer or immunoassay;
    (d) measuring the level of non-nitrated cardiac troponin I in the plasma or serum sample;
    (e) determining a ratio of non-nitrated cardiac troponin I to nitrated cardiac troponin I present in said sample; and
    (f) comparing said ratio with reference values obtained from patients with acute coronary syndrome.

11. The method of claim 10, further comprising treating the subject for acute coronary syndrome.

12. The method of claim 10, further comprising monitoring treatment of the subject for acute coronary syndrome.

13. The method of claim 10 wherein the step of detecting comprises immunoassay.

14. The method of claim 10, which further comprises comparing a concentration of nitrated cardiac troponin I in the sample with a standard curve.

15. A method comprising:
    (a) providing a plasma or serum sample from a human subject who has or is suspected of having cardiac disease selected from the group consisting of acute cardiac ischemia and cardiac ischemia due to chronic coronary artery disease;
    (b) incubating the sample with an antibody suitable for capturing nitrated cardiac troponin I;
    (c) detecting immunocaptured nitrated cardiac troponin I obtained in step (b) by mass spectrometer;
    (d) measuring the level of non-nitrated cardiac troponin I in the plasma or serum sample;
    (e) determining a ratio of non-nitrated cardiac troponin I to nitrated cardiac troponin I present in said sample; and
    (f) comparing said ratio with reference values obtained from patients with cardiac ischemia.

16. A method comprising:
    (a) providing a plasma or serum sample from a human subject who has or is suspected of having cardiac disease selected from the group consisting of acute cardiac ischemia and cardiac ischemia due to chronic coronary artery disease;
    (b) incubating the sample with an antibody suitable for capturing nitrated cardiac troponin I;
    (c) detecting immunocaptured nitrated cardiac troponin I obtained in step (b) by mass spectrometer;
    (d) measuring the level of non-nitrated cardiac troponin I in the plasma or serum sample;
    (e) determining a ratio of non-nitrated cardiac troponin I to nitrated cardiac troponin I present in said sample; and
    (f) comparing said ratio with reference values obtained from patients with acute coronary syndrome.

* * * * *